(12) United States Patent
Mishima et al.

(10) Patent No.: US 6,468,630 B1
(45) Date of Patent: Oct. 22, 2002

(54) ELASTICALLY STRETCHABLE SHEET

(75) Inventors: Yoshitaka Mishima, Kagawa-ken (JP); Yasushi Sayama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 165 days.

(21) Appl. No.: 09/608,222

(22) Filed: Jun. 30, 2000

(30) Foreign Application Priority Data

Jun. 30, 1999 (JP) .............................................. 11-186786

(51) Int. Cl.⁷ .......................... B32B 3/28; D03D 15/08; A61F 13/15
(52) U.S. Cl. ........................ 428/181; 428/182; 442/184; 442/329; 604/384; 604/385.01
(58) Field of Search ................................ 428/182, 181, 428/109; 604/373, 385.01, 385.24, 367, 384; 442/184, 329

(56) References Cited

U.S. PATENT DOCUMENTS

| | | | |
|---|---|---|---|
| 3,243,947 A | * | 4/1966 | Getzin ........................ 428/182 |
| 4,397,704 A | | 8/1983 | Frick .......................... 156/201 |
| 5,681,302 A | | 10/1997 | Melbye et al. ............... 604/373 |

FOREIGN PATENT DOCUMENTS

| | | |
|---|---|---|
| EP | 0119825 | 9/1984 |
| EP | 0321980 | 6/1989 |
| EP | 0556749 | 8/1993 |
| WO | WO 00/37003 | 6/2000 |

* cited by examiner

*Primary Examiner*—Donald J. Loney
(74) *Attorney, Agent, or Firm*—Clark & Brody

(57) ABSTRACT

An elastically stretchable sheet for articles such as diapers and sanitary napkins. A flat sheet material intrinsically having an elastic stretchability in the longitudinal direction rather than in the transverse direction is formed with a plurality of pleats extending in the longitudinal direction and having a plurality of crests and troughs alternately repeating in the transverse direction and a plurality of elastic threads being stretchable in the transverse direction are secured to respective apices of the plurality of crests forming from outer side.

6 Claims, 3 Drawing Sheets

ELASTICALLY STRETCHABLE SHEET

BACKGROUND OF THE INVENTION

This invention relates to a sheet having an elastic stretchability longitudinally and transversely thereof.

It is well known to obtain a nonwoven fabric of comfortable touch by a process comprising the steps of a continuously feeding web of elastically stretchable fiber and treating this with heated emboss-rolls or high pressure column-shaped water streams so that the composite fibers may be heat-sealed together or mechanically intertwined together. Such a nonwoven fabric has conventionally used in various garments such as disposable diapers or sanitary napkins.

In the case of the known nonwoven fabric, the elastic component fibers are apt to be oriented in coincidence with the machine direction during a step of making the web or the subsequent step of treating the web. Consequently, the nonwoven fabric obtained is easily stretchable in the machine direction but often inadequately stretchable in the direction orthogonal to the machine direction.

SUMMARY OF THE INVENTION

It is an object of this invention to make an elastically stretchable sheet being intrinsically stretchable in one direction but not in the direction orthogonal to the one direction stretchable in these two directions.

According to this invention, there is provided a sheet having an elastic stretchability both in a longitudinal direction thereof and in a transverse direction orthogonal to the longitudinal direction, wherein: a flat sheet material intrinsically having a nature of being elastically stretchable in the longitudinal direction without any significant resistance rather than in the transverse direction is formed with a plurality of pleats extending in the longitudinal direction and having a plurality of crests and troughs alternately repeating in the transverse direction and a plurality of elastic members being stretchable in the transverse direction are secured to respective apices of the plurality of crests forming the pleats from outer side.

According to one preferred embodiment of this invention, the elastic members are secured also to respective bottoms of the plurality of troughs forming the pleats from outer side.

According to another preferred embodiment of this invention, the elastic members are provided in the form of elastic threads and according to still another preferred embodiment of this invention, the elastic members are provided in the form of a sheet having an elastic stretchability both in the longitudinal direction and in the transverse direction.

DETAILED DESCRIPTION OF THE PREFERRED EMBODIMENTS

Details of an elastically stretchable sheet according to this invention will be more fully understood from the description given hereunder with reference to the accompanying drawings.

Figure 1:
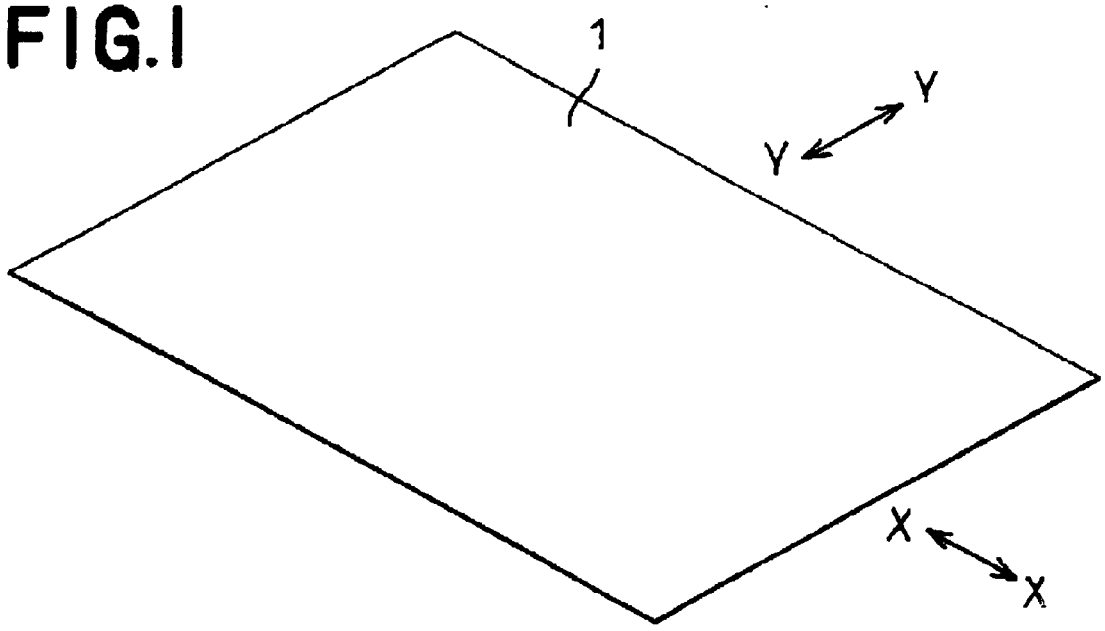
FIG. 1 is a perspective view of a sheet.
Figure 2:
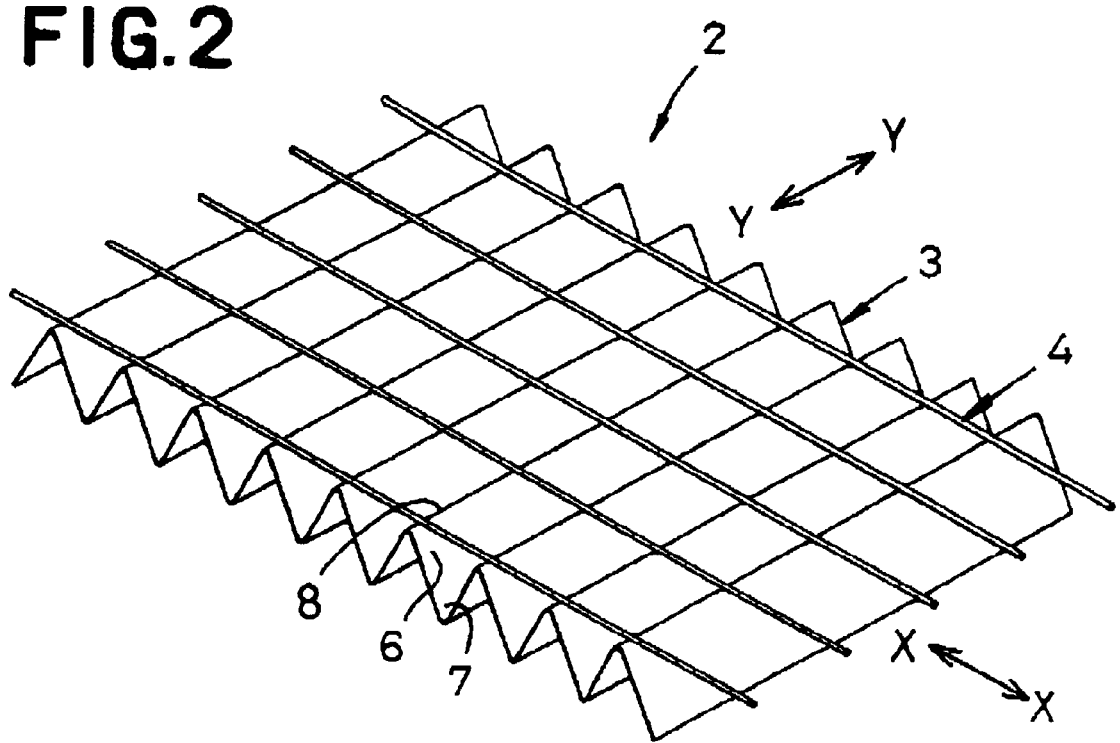
FIG. 2 is a perspective view of an elastically stretchable sheet.

FIG. 1 is a perspective view of a flat sheet material 1 and FIG. 2 is a perspective view of an elastically stretchable sheet 2. In a direction indicated by a double-headed arrow Y, the sheet material 1 is elastically stretchable but in a direction indicated by a double-headed arrow X, the sheet material 1 is not stretchable at all or not easily stretchable as in the direction Y or non-elastically stretchable. Examples of such sheet material 1 include, for example, a nonwoven or woven fabric in which stretchable component yarns such as elastic urethane yarns or crimped conjugated fibers are oriented substantially in the direction Y.

The elastically stretchable sheet 2 comprises a pleated sheet 3 obtained by pleating the sheet material 1 and a plurality of elastic threads 4. The sheet material 1 has alternate crests 6 and troughs 7 each extending in the direction Y to form the pleats undulating in the direction X. The elastic threads 4 rectilinearly extending in the direction X and are respectively bonded with or without a tension to apices 8 of the crests 6.

The elastic threads 4 may be of natural rubber, synthetic rubber, plastic elastomer or the like and secured to the apices 8 by means of suitable adhesive such as hot melt adhesive. It is also possible to use rubber-based hot melt adhesive having an elastic stretchability as the elastic threads 4. The hot melt adhesive extending like the threads may be applied in its molten or semi-molten state to the apices to form the elastic threads 4.

When the elastically stretchable sheet 2 is pulled in the direction Y, the pleated sheet 3 is elastically stretched. When the sheet 2 is pulled in the direction Y, the pleated sheet 3 is flattened and thereby the elastic threads 4 are elastically stretched. Accordingly, the elastically stretchable sheet 2 is elastically stretchable both in the direction Y and in the direction X. The material, the shape and the number of the elastic threads 4 should be selected so that a total stretch stress exhibited by the elastic threads 4 may be substantially equal to a stretch stress exhibited by the pleated sheet 3 when the latter is pulled in the direction Y. Such selection facilitates the elastically stretchable sheet 2 to be elastically stretched uniformly both in the direction Y and in the direction X. The elastically stretchable sheet 2 can be made at a relatively low cost and suitably used as the elastic members in various disposable garments such as disposable diapers.

Figure 3:
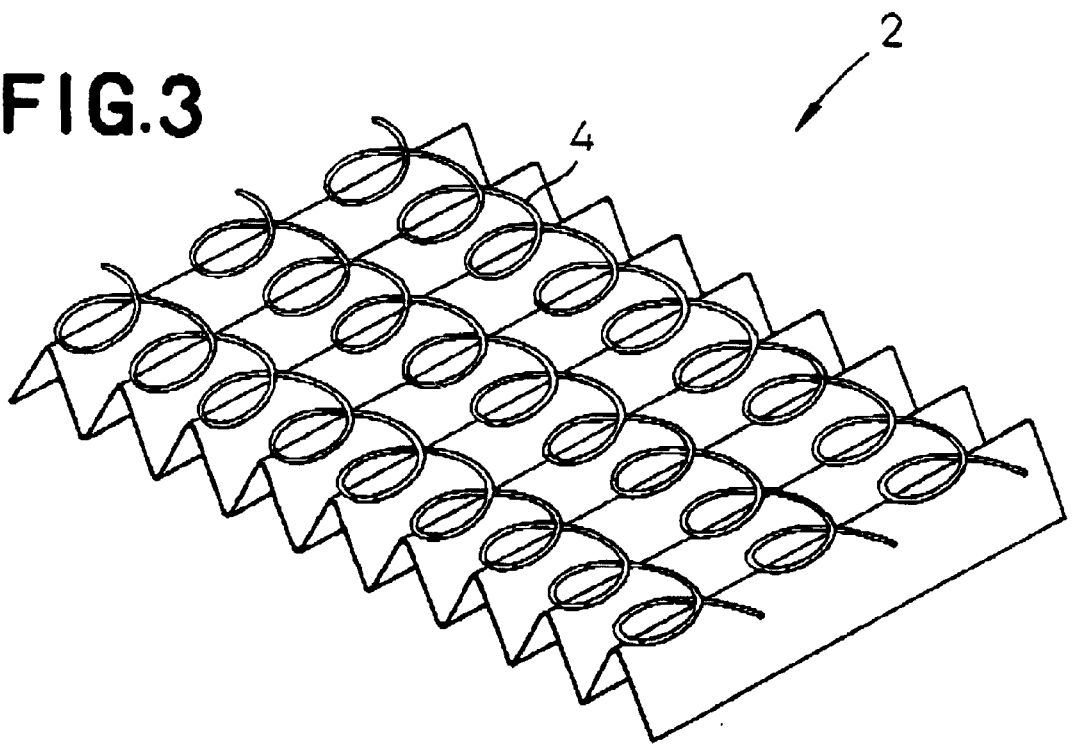
FIG. 3 is a view similar to FIG. 2 but showing one preferred embodiment of this invention.

FIG. 3 is a view similar to FIG. 2 but showing one preferred embodiment of this invention. In the elastically stretchable sheet 2 according to this embodiment, a plurality of elastic threads 4 describe spirals.

Figure 4:
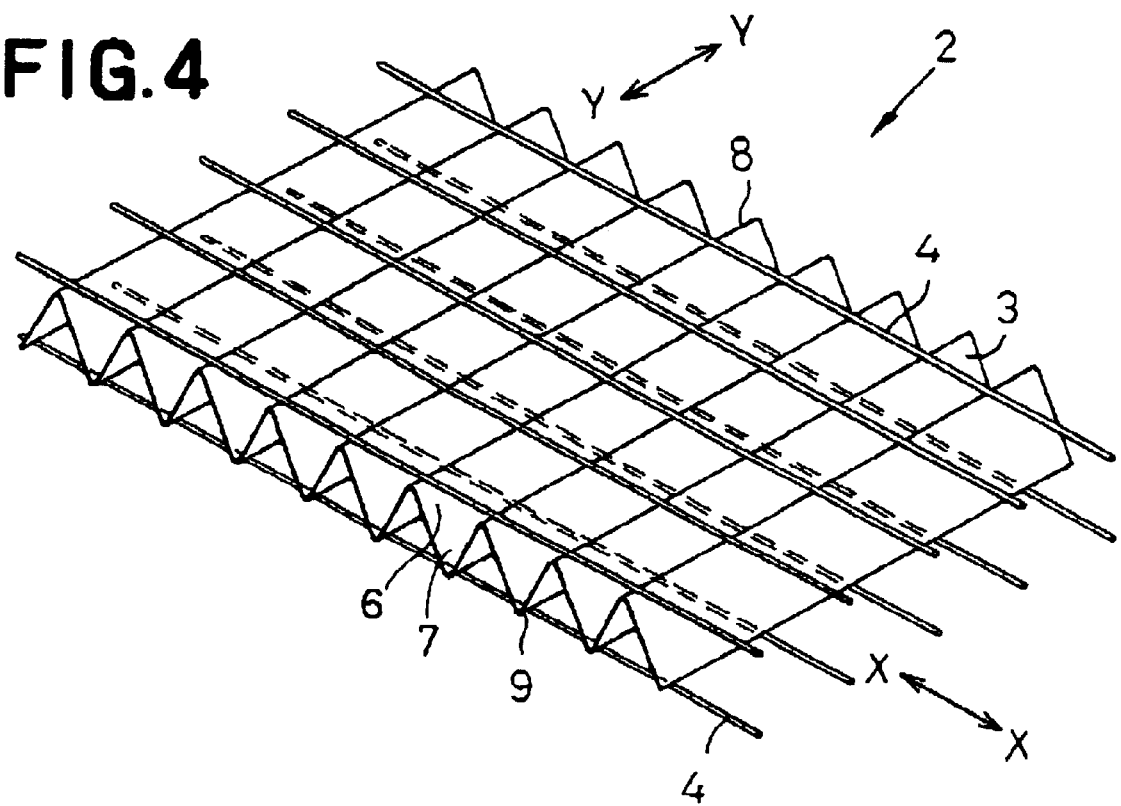
FIG. 4 is a view similar to FIG. 2 but showing another preferred embodiment of this invention.

FIG. 4 also is a view similar to FIG. 2 but showing another preferred embodiment of this invention. In the elastically stretchable sheet 2 according to this embodiment, the plurality of elastic threads 4 rectilinearly extending in the direction X are secured not only to the apices 8 of the crests 6 from outer side (i.e., from above as viewed in FIG. 4) but also to bottoms 9 of the troughs 7 from outer side (i.e., from below as viewed in FIG. 4.

Figure 5:
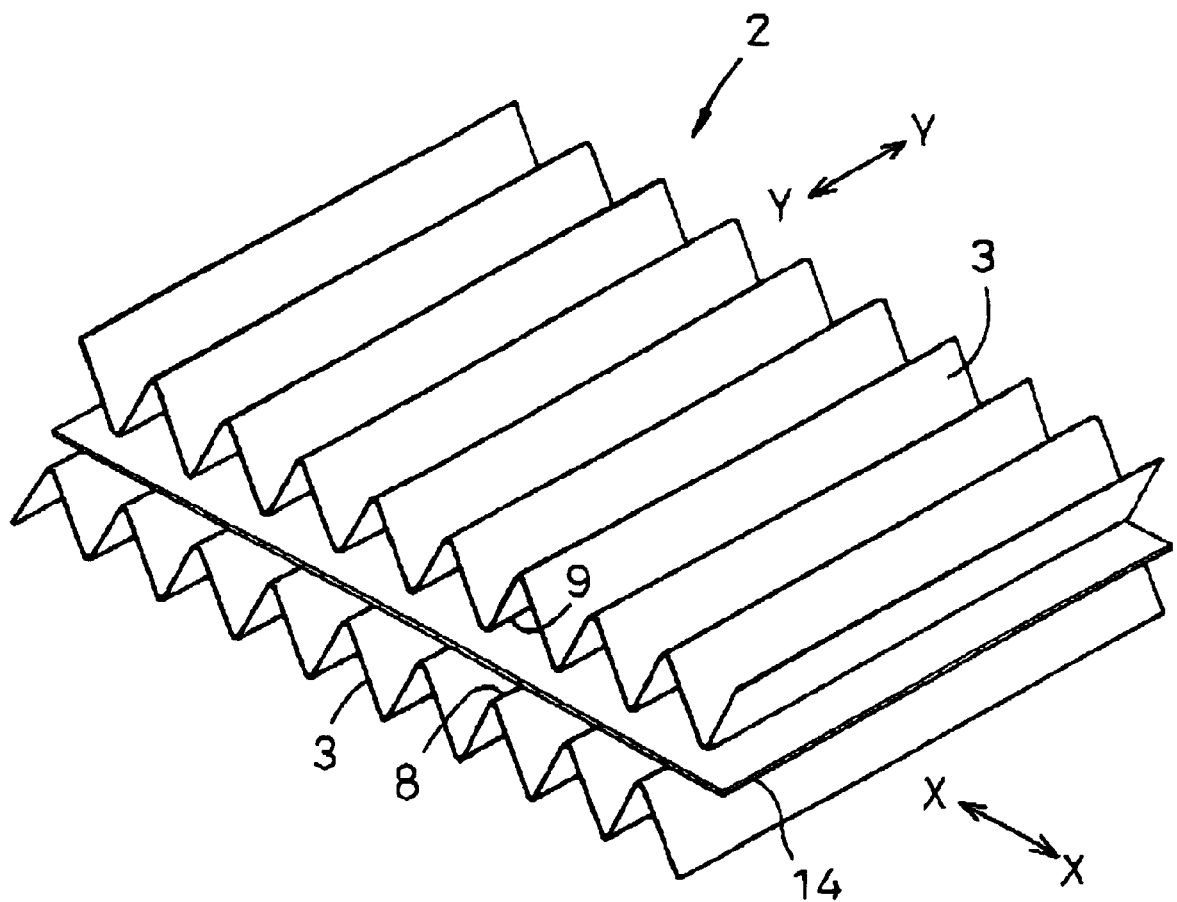
FIG. 5 is a view similar to FIG. 2 but showing still another preferred embodiment of this invention.

FIG. 5 also in a view similar to FIG. 2 but showing still another preferred embodiment of this invention. The elastically stretchable sheet 2 according to this embodiment comprises a pair of pleated sheets 3, 3 placed upon each other and an elastic sheet 14 being elastically stretchable both in the direction Y and in the direction X disposed between said two pleated sheets 3, 3. The elastic sheet 14 is secured to a bottom 9 of the upper pleated sheet 3 and to an apice 8 of the lower pleated sheet 3 by means of hot melt adhesive (not shown). As according to this embodiment, the elastic threads 4 in FIGS. 2–4 may be replaced by the elastic sheet 14.

In the case of the pleated sheet 3 according to this invention, there is no distinction between its upper and lower surfaces and the crests 6 of the peats may be designated as the troughs 7 of the pleats substantially without any confusion.

This invention enables the sheet material which is elastically stretchable with no significant resistance only in one direction to be elastically stretchable with no significant resistance also in another direction orthogonal to the one direction.

What is claimed is:

1. A sheet having an elastic stretchability both in a longitudinal direction thereof and in a transverse direction orthogonal to said longitudinal direction, wherein:

a flat sheet of material intrinsically having a nature of being elastically stretchable in said longitudinal direction but not elastically stretchable in the transverse direction, the flat sheet formed with a plurality of pleats extending in said longitudinal direction and having a plurality of crests and troughs alternately repeating in said transverse direction; and a plurality of elastic members extending and being stretchable in the transverse direction and being bonded to respective apices of said plurality of crests.

2. The sheet according to claim 1, wherein said elastic members are bonded also to respective bottoms of said plurality of troughs.

3. The sheet according to claim 1, wherein said elastic members are provided in the form of elastic threads.

4. The sheet according to claim 1, wherein said elastic members are provided in the form of a sheet having an elastic stretchability both in said longitudinal direction and in said transverse direction.

5. The sheet according to claim 1, wherein said sheet is for a disposable diaper or a sanitary napkin.

6. The sheet according to claim 1, wherein said elastic members are spiral threads.

\* \* \* \* \*